US010214485B2

(12) United States Patent
Spielmann et al.

(10) Patent No.: US 10,214,485 B2
(45) Date of Patent: Feb. 26, 2019

(54) METHOD OF REPROCESSING ALKANESULFONIC ACID

(71) Applicant: BASF SE, Ludwigshafen am Rhein (DE)

(72) Inventors: Jan Spielmann, Mannheim (DE); Michael Koch, Speyer (DE); Juergen Wortmann, Limburgerhof (DE); Sabine Weiguny, Freinsheim (DE); Feelly Ruether, Frankenthal (DE); Robert Sengpiel, Aachen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/774,722

(22) PCT Filed: Nov. 8, 2016

(86) PCT No.: PCT/EP2016/076963
§ 371 (c)(1),
(2) Date: May 9, 2018

(87) PCT Pub. No.: WO2017/080994
PCT Pub. Date: May 18, 2017

(65) Prior Publication Data
US 2018/0327352 A1    Nov. 15, 2018

(30) Foreign Application Priority Data

Nov. 10, 2015 (EP) .................................. 15193897

(51) Int. Cl.
*C07C 303/44* (2006.01)
(52) U.S. Cl.
CPC .................................. *C07C 303/44* (2013.01)
(58) Field of Classification Search
CPC .................................................. C07C 303/44
See application file for complete search history.

(56) References Cited

U.S. PATENT DOCUMENTS 4,035,242 A    7/1977    Brandt
4,450,047 A    5/1984    Malzahn
(Continued)

FOREIGN PATENT DOCUMENTS

CN          1810780 A        8/2006
DE     197 43 901 C1         4/1999
(Continued)

OTHER PUBLICATIONS

Craig et al, Journal of the American Chemical Society, Cryoscopic Studies in Methanesulfonic Acid, 1950, 72, pp. 163-166. (Year: 1950).*

(Continued)

*Primary Examiner* — Paul A Zucker
(74) *Attorney, Agent, or Firm* — Oblon, McClelland, Maier & Neustadt, L.L.P.

(57) ABSTRACT

The invention relates to a method of reprocessing alkanesulfonic acid employed in a chemical process as an agent, catalyst or solvent and comprising the steps of:
(a) removing an alkanesulfonic acid-comprising stream from a reaction mixture generated in the chemical process,
(b) feeding the alkanesulfonic acid-comprising stream into a melt crystallization as the starting melt to form crystals of the alkanesulfonic acid, of hydrates of the alkanesulfonic acid or of a mixture of both suspended in mother liquor,
(c) performing a solid-liquid separation to remove the crystals from the mother liquor,
(d) optionally washing the crystals to remove mother liquor adhering to the crystals,
(e) recycling the washed or unwashed crystals removed from the mother liquor into the chemical process.

15 Claims, 2 Drawing Sheets

(56) References Cited

U.S. PATENT DOCUMENTS

| | | | |
|---|---|---|---|
| 4,921,966 A | | 5/1990 | Stegmann et al. |
| 4,938,846 A | | 7/1990 | Comstock et al. |
| 5,284,993 A | | 2/1994 | Eastman |
| 5,589,691 A | * | 12/1996 | Venkataramani ..... C07F 9/3873 |
| | | | 252/182.11 |
| 6,060,621 A | | 5/2000 | Biertuempel et al. |
| 6,337,421 B1 | | 1/2002 | Gancet |
| 6,531,629 B1 | | 3/2003 | Eiermann et al. |
| 7,045,654 B2 | | 5/2006 | Hobbs |

FOREIGN PATENT DOCUMENTS

| | | |
|---|---|---|
| DE | 600 00 764 T2 | 7/2003 |
| EP | 0 323 402 A1 | 7/1989 |
| EP | 0 373 305 A1 | 6/1990 |
| EP | 0 505 692 A1 | 9/1992 |
| EP | 0 675 107 A1 | 10/1995 |
| EP | 0 906 904 A2 | 4/1999 |
| GB | 1 350 328 | 4/1974 |
| WO | WO 00/31027 A1 | 6/2000 |
| WO | WO 02/074720 A2 | 9/2002 |
| WO | WO 2013/061336 A2 | 5/2013 |
| WO | WO 2015/086645 A1 | 6/2015 |

OTHER PUBLICATIONS

Berthoud, A., "Quelques Propriétés Physico-chimiques des acides éthane-et methane-sulfonique", Velv. Chim. Acta, vol. 12, 1929, pp. 859-865.

Luong, B.X., et al., "Use of methanesulfonic acid as catalyst for the production of linear alkylbenzenes", Journal of Catalysis, vol. 226, 2004, pp. 301-307.

Craig, R.A., et al., "Cryoscopic Studies in Methanesulfonic Acid", Journal of the American Chemical Society, vol. 72, 1950, pp. 163-166.

Takeuchi, S., et al., "Selective Synthesis of Gas Oil via Oligomerization of Light Olefins Catalyzed by Methanesulphonic Acid", Journal of the Japan Petroleum Institute, vol. 50 No. 4, 2007, pp. 188-194 (with English abstract).

Tian, Y., et al., "A Novel Application of Methanesulfonic Acid as Catalyst for the Alkylation of Olefins with Aromatics", Industrial & Engineering Chemistry Research, vol. 51, pp. 13627-13631.

Zhao, Z., et al., "An efficient method for the alkylation of α-methylnaphthalene with various alkylating agents using Methanesulfonic acid as novel catalysts and solvents", Catalysis Letters, vol. 102, No. 3-4, Aug. 2005, pp. 219-222.

* cited by examiner

METHOD OF REPROCESSING ALKANESULFONIC ACID

The invention proceeds from a method of reprocessing alkanesulfonic acid employed in a chemical process as an agent, catalyst or solvent.

One field of application for alkanesulfonic acid, in particular methanesulfonic acid (MSA), is the catalytic alkylation of benzene or substituted benzene with olefins to produce linear alkylbenzene. This in turn is a starting material for the production of linear alkylbenzenesulfonic acids, the most commonly used surfactants.

The catalysts typically employed in the production of linear alkylbenzenes include, for example, boron trifluoride, aluminum trichloride, sulfuric acid or hydrofluoric acid. Among these, hydrofluoric acid is the most commonly employed catalyst despite its corrosivity, toxicity and volatility and the accompanying considerable maintenance, safety and disposal problems for plant operation.

WO-A 2013/061336 discloses that methanesulfonic acid may be employed as an alternative catalyst in the production of linear alkylbenzenes. This document deems it necessary to recover, rather than dispose of, the methanesulfonic acid once it has been used in the production of the linear alkylbenzenes. However, maintaining the catalytic activity of the recovered methanesulfonic acid to a sufficient extent is problematic. The problem here is that during the catalytic reaction the methanesulfonic acid absorbs impurities which can reduce catalytic activity. It does not follow from WO-A 2013/061336 how removal of the impurities might be effected to retain the catalytic activity.

In addition to production of linear alkylbenzene, alkanesulfonic acids may also be employed as an acidic catalyst in other chemical processes, in particular alkylations and esterification reactions. Thus, for example, established acidic catalysts such as sulfuric acid, para-toluenesulfonic acid or hydrofluoric acid may be replaced to functionally largely identical effect. The advantage of alkanesulfonic acid, in particular methanesulfonic acid, is its improved catalytic efficacy or, compared to HCl, its far lower toxicity.

The use of methanesulfonic acid as catalyst in the alkylation of salicylic acids is disclosed in, for example, U.S. Pat. No. 7,045,654 and the use as catalyst in the alkylation of monocyclic aromatics with α-olefins is disclosed in WO-A 02/074720. Both of these documents describe that the removed methanesulfonic acid-comprising phase exhibits dark/brown discoloration on account of color-conferring components formed in the reaction.

EP-A 323402 describes a method of producing liquid, alkylated 2-(2-hydroxyphenyl)benzotriazole mixtures with methanesulfonic acid as catalyst. The α-olefins employed as alkylating agents are preferably slowly added under the surface of the reaction medium to reduce formation of secondary components such as oligomers of the α-olefins. The reaction is preferably conducted at high temperatures of 170-180° C. The methanesulfonic acid-comprising phase separates off after reaction of the product phase. The reaction forms colored compounds which remain in the product phase and the methanesulfonic acid-comprising phase.

Takahashi et al., J. Jpn. Petrol. Inst. Vol. 50, No. 4, 2007, pages 188-194 describes the methanesulfonic acid-catalyzed oligomerization of light olefins, such as ethylene, propylene, 1-butene and isobutene to form liquid hydrocarbons in a continuous flow reactor under high pressures of $3 \cdot 10^5$ Pa at 20° C. to 40° C. At the end of the reaction the liquid hydrocarbons formed are removed from the methanesulfonic acid employed as catalyst by phase separation. In this process an elevated concentration of water in methanesulfonic acid has a negative impact on the yield of hydrocarbons. The phase comprising the removed methanesulfonic acid exhibits dark discoloration due to color-conferring components formed.

The above-referenced documents show that in methanesulfonic acid-catalyzed reactions of olefins color-conferring compounds may form even at very low temperatures and may accumulate in the hydrocarbon-containing product phase and also in the methanesulfonic acid phase. Reuse of the methanesulfonic acid without a preceding purification step may consequently result in contents of color-conferring components in the product phase that are no longer tolerable.

Since alkanesulfonic acids, in particular methanesulfonic acid, are substances of substantially greater value than the acids hitherto employed as catalysts, recovery and repeated use is imperative for economic utilization. In this regard it has been found that simple recycling without purification results in a reduction in conversion in the reaction system with catalytic utilization of the methanesulfonic acid.

A methanesulfonic acid-catalyzed alkylation of aromatics with olefins intended to remove olefinic compounds from aromatic hydrocarbons is described in Tian et al., Ind. Eng. Chem. Res., Vol. 51, 2012, pages 13 627-13 631. The hydrophilic methanesulfonic acid-containing phase is reused as catalyst after removal without a purification step. Here, a reduction in catalytic activity is observed with every recycling cycle. After the fifth recycling cycle the conversion had fallen from 90% to 66%.

Zhao et al., Catalysis Letters, Vol. 102, 2005, pages 219-222 describes the methanesulfonic acid-catalyzed alkylation of α-methylnaphthalene with alkenes. After phase separation the hydrophilic methanesulfonic acid-containing phase is recycled into the process without purification. After only two recycling cycles conversion after 120 minutes was observed to decline from 92.8% to 86.5%.

In addition to use as a catalyst alkanesulfonic acid may also be employed as solvent in a chemical production process. Reaction mixtures comprising alkanesulfonic acid are generally biphasic and separate into a hydrophilic phase and a hydrophobic phase once reaction has ended. The alkanesulfonic acid employed is then substantially in the hydrophilic phase and impurified with low boilers and high boilers. Here too it is necessary to purify the alkanesulfonic acid before recycling into the chemical process.

Possible methods of purifying alkanesulfonic acid are described in particular in connection with the method of producing alkanesulfonic acids.

For example, WO-A 00/31027 discloses the production of alkanesulfonic acid by oxidation of alkyl mercaptans, dialkyl disulfides or dialkyl polysulfides with nitric acid. This generates nitrogen oxides, water and further byproducts such as sulfuric acid. The nitric acid is regenerated from the nitrogen oxides by oxidation with oxygen and recycled into the process. To purify the product, low boilers and high boilers are removed by distillation in two stages to obtain pure, practically anhydrous alkanesulfonic acid. Water and nitric acid are removed from the crude product in a water removal column operated as a stripping column at slightly reduced pressure. The bottoms product comprises 1 wt % water and about 1 wt % high boilers, especially sulfuric acid. The removal of the high boilers is achieved by distillation of the alkanesulfonic acids with purities of greater than 99.5 wt % and sulfuric acid contents of less than 50 ppm under high vacuum, i.e. at a pressure of from 0.1 to 20 mbar (abs).

WO 2015/086645 describes the production of methanesulfonic acid by oxidation of dialkyl sulfides with nitrogen oxides. The nitrogen oxides are regenerated with oxygen-enriched air for example. The reaction products are subsequently freed of low and high boilers via two distillation columns. The thus purified product comprises an unspecified concentration of methanesulfonic acid.

GB-A 1350328 describes the synthesis of alkanesulfonic acids by chlorination of alkyl mercaptans or dialkyl disulfides in aqueous HCl. The product of the reaction is alkanesulfonic acid in 70 to 85 wt % purity. This document describes a two-stage process for producing anhydrous methanesulfonic acid. This comprises a first step in which water is distilled off and a second step in which the methanesulfonic acid is distilled out of the bottoms product with a short column and obtained overhead.

CN-A 1810780 describes the synthesis of methanesulfonic acid by reaction of ammonium sulfite with dimethyl sulfate. This affords ammonium methylsulfonate and ammonium sulfate. Addition of calcium hydroxide forms soluble calcium methylsulfonate and insoluble calcium sulfate which may be removed easily. Sulfuric acid is added to liberate methanesulfonic acid and once again form and precipitate calcium sulfate. The aqueous solution formed is initially subjected to distillation to remove water and then subjected to distillation under reduced pressure to obtain methanesulfonic acid.

DE-C 197 43 901 describes the synthesis of methanesulfonic acid by reaction of sulfite ions with dimethyl sulfate. These sulfite ions are reacted in an aqueous system at elevated temperature and exposed to a strong acid. Sulfate is formed as a byproduct, for example in the form of sodium sulfate. Purification of the acid is by distillation.

EP-A 0 675 107 describes a process for continuous production of alkanesulfonyl chloride (ASC) or alkanesulfonic acid (ASA) by reacting an alkane mercaptan or a dialkane disulfide with chlorine in aqueous hydrochloric acid at elevated pressure. HCl and other low boilers not condensable under the process conditions are desorbed after decompression of the superatmospheric pressure. ASC is produced at a preferred temperature range of from 10° C. to 35° C. and purified by means of a distillation column. ASA is obtained from ASC by hydrolysis at temperatures of from greater than 80° C. to 135° C. in the presence of water. The purification of ASC and/or ASA is also carried out with a vapor stripper for example, residual ASC also being hydrolyzed therein.

The removal of water from aqueous methanesulfonic acid by evaporation of the water in a falling film evaporator at reduced pressure is described in U.S. Pat. No. 4,450,047. Water is drawn off overhead and a product stream comprising more than 99.5 wt % methanesulfonic acid is obtained.

U.S. Pat. No. 4,938,846 discloses the removal of water from aqueous methanesulfonic acid by evaporation of the water in two falling-film evaporators arranged in series and both operated at reduced pressure.

The disadvantage of the prior art distillation methods is that the process is highly energy intensive on account of the high temperatures and the required reduced pressure. In addition, it is not possible to remove high boilers such as sulfuric acid without particularly energy-intensive conversion of the alkanesulfonic acid into the gas phase. Also, certain purification processes achieve the distillation task with falling film evaporators which are useable on a large industrial scale only with difficulty.

U.S. Pat. No. 4,035,242 discloses a likewise very energy intensive method where aqueous methanesulfonic acid is purified in a two-stage distillation process. In the first distillation column a large part of the water is removed as a low boiler at reduced pressure. The bottoms product comprising methanesulfonic acid is evaporated and separated in a second rectification column at reduced pressure to obtain the methanesulfonic acid.

U.S. Pat. No. 6,337,421 discloses the removal of sulfuric acid from methanesulfonic acid using basic anion exchange resins. Other methods of removing sulfuric acid are also described, for example distillation or fractionating crystallization and also separation by nanofiltration, but none of these achieve adequate results according to the description of U.S. Pat. No. 6,337,421.

The purification of methanesulfonic acid comprising oxidizable compounds is described in EP-A 0 505 692 and EP-A 0 373 305. EP-A 0 505 692 discloses supplying chlorine to convert the impurities into methanesulfonyl chloride which is hydrolyzed to afford methanesulfonic acid and HCl in a further step. EP-A 0 373 305 discloses supplying ozone which converts methyl thiosulfate into methanesulfonic acid. However, the disadvantage of these two methods is that high-boiling components such as sulfuric acid cannot be removed with the result that further purification steps are necessary.

The fractionating crystallization of methanesulfonic acid and also of ethanesulfonic acid is known in principle from R. A. Craig et al., J. Am. Chem. Soc., 1950, Vol. 72, pages 163 to 164 or A. Berthoud, Helv. Chim. Acta, 1929, Vol. 12, page 859, but no indication is given as to how the methods described therein could be implemented on a large-industrial scale.

In contrast to impurities arising from production of the alkanesulfonic acids, an alkanesulfonic acid, in particular methanesulfonic acid, employed in a chemical process may comprise further impurities. These are typically distinguished into low boilers and high boilers, the boiling point of low boilers being below the boiling point of alkanesulfonic acid and the boiling point of the high boilers being above the boiling point of alkanesulfonic acid.

Typical low boilers that may be present in an alkanesulfonic acid employed in chemical processes include, for example, water, nitric acid, hydrogen chloride, chlorine, alkyl mercaptans, dialkyl disulfides, dialkyl polysulfides, methyl methanesulfonate (MMS), sulfur dioxide, ammonia, dimethyl sulfate, monomethyl sulfate, short-chain hydrocarbons, olefins, aromatic hydrocarbons, benzene, short-chain aliphatic and aromatic alcohols, esters of methylsulfonic acid, aromatic sulfonic acids, alkylsulfonic acids, carboxylic acids and carboxylic esters.

Examples of high boiler impurities that may be present include sulfuric acid, salts, for example sodium sulfate, sodium hydrogensulfate, sodium methylsulfate, ammonium sulfite, ammonium methylsulfate, ammonium sulfate, calcium hydroxide, calcium sulfate and calcium methylsulfate, long-chain hydrocarbons, aromatic hydrocarbons, olefins, long-chain aliphatic alcohols, aromatic alcohols, esters of methylsulfonic acid, aromatic sulfonic acid, alkylsulfonic acids, carboxylic acids or carboxylic esters.

In addition to the abovementioned impurities other unidentified or unidentifiable high boilers, in particular color-conferring substances (color givers), may also be present.

EP-A 323402 discloses a method of producing liquid, alkylated 2-(2-hydroxyphenyl)benzotriazole mixtures with methanesulfonic acid as catalyst. In one embodiment of the method the reaction mixture is mixed with water once reaction has ended. The crude product phase is subsequently separated from the methanesulfonic acid-containing phase. From the methanesulfonic acid-containing phase the methanesulfonic acid is worked up by distillation and recycled into the process. This distillation is a multistage distillation. In the first distillation stage water is removed and the methanesulfonic acid is ultimately distilled overhead.

U.S. Pat. No. 5,284,993 describes the regeneration of an alkylation catalyst for alkylating olefinic hydrocarbons with isoparaffinic hydrocarbons consisting of strong acids such as fluorosulfonic acid and methanesulfonic acid. The catalyst is impurified with so-called acid-soluble oils which are undesired byproducts of the acid-catalyzed alkylation reaction. It is described that an excessively high concentration of these acid-soluble oils has a negative effect on the activity of the catalyst and the product being formed. To regenerate the catalyst the strong acid is removed in a first step by a flash distillation. Water is then added to the mixture of methanesulfonic acid and acid-soluble oils until phase separation is achieved. The phases are separated into a hydrophobic phase comprising acid-soluble oils and a hydrophilic phase comprising methanesulfonic acid and water. Water is removed from the hydrophilic phase by a process not further described here and the methanesulfonic acid is recycled into the alkylation process.

WO-A 2013/061336 describes a process for producing linear alkylbenzene from a $C_{10}$-$C_{14}$-alkene with excess benzene in which methanesulfonic acid is cited as a catalyst. The process description also refers to a unit for catalyst recovery without disclosing the mode of operation of this process step. The reactants are fed together with an alkane mixture as solvent to an alkylation step. The reaction mixture is subsequently separated into waste streams, recycle streams and product streams in a separation device. The separation device comprises, for example, two phase separators and a distillation device. The reaction mixture is biphasic and once reaction has ended separates in the first phase separator into a hydrophobic phase and a hydrophilic catalyst phase. The hydrophobic phase may be freed of residual catalyst by washing with water or an alkyl solution. Said phase is subsequently separated by distillation to obtain the product. The benzene removed in the distillation and the alkanes and unconverted olefins are recycled into the alkylation step. Used catalyst and water are discharged via a further takeoff. The hydrophilic, methane sulfonic acid-comprising phase withdrawn from the first phase separator is either recycled directly into the process or fed into a unit for catalyst recovery not further described in WO-A 2013/061336.

The formation of dodecylbenzene from benzene and 1-dodecene with methanesulfonic acid as catalyst in a solvent-free reaction system was investigated by B. X. Luong et al. in Journal of Catalysis, Vol. 226, 2004, pages 301-307. It was shown that direct recycling of the methanesulfonic acid-containing catalyst phase resulted in unacceptable, severe drop in activity of the methanesulfonic acid even after just a few recycling cycles. This reactivity drop is believed to be due to the presence of more than 0.25 wt % of water and of catalytically-inhibiting, high-boiling products accumulating in the catalyst phase. To reestablish the catalytic activity of the methanesulfonic acid the methanesulfonic acid-comprising phase is diluted with water and extracted with dichloromethane. The water is then removed by distillation. The introduction and the required removal of additional water and of the solvent dichloromethane result in a highly complex, multistage purification process for the methanesulfonic acid.

The disadvantage of all of the methods known from the prior art is that they either require very high capital expenditure and/or large energy inputs to remove the impurities or that due to the impurities present in the recycled alkanesulfonic acid the catalytic activity, and thus the conversion in the chemical process employing alkanesulfonic acid as catalyst, declines.

The reactivity of the alkanesulfonic acid in distillation processes also needs to be taken into account. Alkanesulfonic acids can react with organic substances, for example olefins or aromatics, in manifold ways. Depending on the reaction conditions and the type of the organic reactants this can form decomposition products of alkanesulfonic acid, for example the methyl ester of methanesulfonic acid, sulfur dioxide or $H_2S$. Takeuchi et al., J. of the Japan Petroleum Institute, Vol. 50(4), 2007, pages 88-194 describes the formation of oligomers of volatile olefins with methanesulfonic acid. With less volatile aromatic olefins, which are also present in the process for producing linear alkylbenzenes (LAB process), a reaction of the methanesulfonic acid with the olefins to form dark products in the distillation bottoms is observed. Above 150° C. and at longer reaction times as are typical in continuous chemical production methods, even high-viscosity, tar-like products are formed. The reaction is promoted by the use of a high temperature and a low concentration of water. However, these are precisely the conditions found in a distillative purification operation for alkanesulfonic acid. For example, achieving sufficient catalytic activity of the methanesulfonic acid requires a water content of less than 1 wt %. In order to be able to achieve this concentration by distillation, at moderate subatmospheric pressures of about 0.1 bar (abs) temperatures of about 190° C. are required. These conditions in the bottoms of a distillation result in massive formation of dark high boilers which render impracticable a solitary distillation process step for purification of methanesulfonic acid in a method that recycles methanesulfonic acid. Distillation of the methanesulfonic acid overhead requires yet higher temperatures and/or requires low pressures which entail great cost and complexity. While such a distillation regime affords pure methanesulfonic acid at the top of a distillation column, it is very energy-intensive, results in yield losses and leaves behind highly impurified, high-boiling olefins in the bottoms of the distillation.

The present invention accordingly has for its object the provision of a method of reprocessing alkanesulfonic acid employed in a chemical process as an agent, catalyst or solvent which may be carried out with relatively low capital expenditure and relatively low energy use.

The object is achieved by a method of reprocessing alkanesulfonic acid employed in a chemical process as an agent, catalyst or solvent and comprising the steps of:
(a) removing an alkanesulfonic acid-comprising stream from a reaction mixture generated in the chemical process,
(b) feeding the alkanesulfonic acid-comprising stream into a melt crystallization as the starting melt to form crystals of the alkanesulfonic acid, of hydrates of the alkanesulfonic acid or of a mixture of both suspended in mother liquor,
(c) performing a solid-liquid separation to remove the crystals from the mother liquor,
(d) optionally washing the crystals to remove mother liquor adhering to the crystals,
(e) recycling the washed or unwashed crystals removed from the mother liquor into the chemical process.

It has now been found that, surprisingly, the melt crystallization makes it possible to remove impurities from the alkanesulfonic acid in amounts sufficient to allow said acid to be reused in the chemical process without an appreciable decline in conversion in the chemical process while additionally reducing the necessary energy requirement compared to the prior art method of purifying the alkanesulfonic acid.

Impurities are generally present in the form of low boilers or high boilers. The term "low boilers" is to be understood as meaning water and all components having a boiling point below the boiling point of alkanesulfonic acid. The term "high boilers" is to be understood as meaning all components having a boiling point above the boiling point of alkanesulfonic acid. The alkanesulfonic acid is in particular methanesulfonic acid.

Another advantage is that, in contrast to hitherto employed methods of distillative purification of alkanesulfonic acid, the method according to the invention makes it possible to achieve high purities in simple fashion in particular in the purification of methanesulfonic acid. The method according to the invention moreover removes the majority of high boilers from the alkanesulfonic acid which is achieved in the prior art only through energy intensive distillation by converting the alkanesulfonic acid into the gas phase. However, this conversion of the alkanesulfonic acid, in particular methanesulfonic acid, has the further disadvantage that said acid is highly corrosive under the conditions in the gaseous distillation thus necessitating the use of complex, corrosion-resistant apparatuses.

In order to be able to recover the alkanesulfonic acid, it is necessary in a first step to initially remove said acid from the reaction mixture generated in the chemical process. To this end it is possible, for example, to add water, the alkanesulfonic acid being transferred into the aqueous phase in this case. Alternatively, many applications, for example the production of linear alkylbenzenes, in which the alkanesulfonic acid is used as catalyst in any case generate a biphasic reaction mixture having a hydrophilic phase and a hydrophobic phase. In these cases in which the reaction mixture is biphasic or a second phase is generated by addition of water, the alkanesulfonic acid-comprising stream is preferably removed from the reaction mixture by phase separation. This may be achieved using any apparatuses for phase separation known to those skilled in the art. Alternative methods are, for example, extractive or chromatographic methods. However, these have the disadvantage of low selectivity or are very costly and complex.

The crystallization causes the impurities to be removed from the alkanesulfonic acid and to accumulate in the mother liquor. However, since the mother liquor still comprises a large proportion of uncrystallized alkanesulfonic acid it is preferable when the mother liquor after removal of the crystals in step (c) and/or the mother liquor generated in step (b) is at least partly recycled into the melt crystallization in step (b).

Depending on the water content in the alkanesulfonic acid-comprising stream fed to the melt crystallization either alkanesulfonic acid or the hydrate of alkanesulfonic acid crystallizes. Since both the crystallization of methanesulfonic acid and the crystallization of the hydrate of alkanesulfonic acid require a certain water content in the melt, this may require that the water content is adjusted before the alkanesulfonic acid-comprising stream is fed into the melt crystallization in step (b). Particularly when alkanesulfonic acid and not the hydrate is employed in the chemical process this may require that the water is removed from the alkanesulfonic acid-comprising stream before crystallization. Since water is a low boiler compared to alkanesulfonic acid the alkanesulfonic acid-comprising stream may to this end, for example, before being fed into the melt crystallization in step (b) be distilled to remove low boilers, wherein the low boilers are drawn off at the top of a distillation column and a material stream comprising alkanesulfonic acid, high boilers and residual low boilers is withdrawn at the bottom of the distillation column and the stream comprising alkanesulfonic acid, high boilers and residual low boilers is fed to the melt crystallization in step (b). Alternatively, in the case of an insufficient water content it may also be necessary to add water. This is the case particularly when the monohydrate of alkanesulfonic acid is to be crystallized.

When the alkanesulfonic acid, in particular methanesulfonic acid, recovered from a chemical process has an excessive water content, for example with resulting insufficient catalytic activity, the water content is to be lowered by low boilers removal to, for example, below 1 wt % to achieve sufficient catalytic activity.

Here, by employing a crystallization, the water content may be adjusted advantageously compared to a purely distillative low boilers removal by two alternative methods.

On the one hand, it is possible by distillative low boiler removal to reduce the water content of the alkanesulfonic acid-containing melt to not more than 25 mol % based on the amount of water and alkanesulfonic acid and then obtain pure alkanesulfonic acid having a water content below 1 wt % by melt crystallization. This can save energy in the distillation and also subject the bottoms to reduced thermal stress with the advantage that fewer additional impurities are formed by reaction of the alkanesulfonic acid with impurities already present.

A low boilers removal may be conducted, for example, by distillation to prepare pure methanesulfonic acid at temperatures below 150° C. and moderate reduced pressures of about 50 to 150 mbar in order that little energy needs to be expended and the water content is only reduced to 4 wt % in the bottoms. These conditions do not result in significant reaction of the methanesulfonic acid with, for example, aromatic olefins to afford very dark products. Both the residual water and dark products may be largely removed by a subsequent crystallization.

By contrast, a purely distillative reduction of the water concentration to less than 1 wt % at 190° C. and 100 mbar results in greater formation of secondary components on account of the higher temperature.

On the other hand the alkanesulfonic acid-containing melt recovered from a chemical process may be directly crystallized and then fed to a low boilers removal. This method is advantageous particularly when, for example, by a low boilers removal or water addition the concentration of the methanesulfonic acid-containing melt is adjusted to 31 to 75 mol %, preferably from 45 to 63 mol % and particularly preferably from 47 to 55 mol % and methanesulfonic acid hydrate is crystallized. A subsequent low boilers removal to achieve a concentration below 1 wt % and a sufficient catalytic activity may be carried out without the possibility of additional impurities being formed in the low boilers removal since impurities capable of acting as reactants for the alkanesulfonic acid are largely absent.

Since a crystallization and subsequent solid-liquid separation cannot generally achieve complete removal of the product from the starting melt, the mother liquor exiting the crystallizer still comprises a large proportion of product. It is therefore preferable when the alkanesulfonic acid-depleted mother liquor exiting the crystallizer is completely or at least partly recycled back into the reprocessing process or else into purification stages of the chemical process. In the case of recycling into the reprocessing process, the alkanesulfonic acid-depleted mother liquor may be returned either into the crystallizer, referred to as the crystallization cycle, or else back into the distillation for removal of the low boilers, referred to as the distillation cycle. Recycling into the distillation has the advantage that low boilers which accumulate in the mother liquor due to removal of the product are likewise removed.

It is preferable when the entirety of the mother liquor which is removed from the crystallizate in step (c) or runs off from the crystallizer is recycled into the distillation for removing low boilers or into the melt crystallization.

When the washing of the crystals in step (d) is additionally carried out, impurified washing liquid is generated which is recycled into the process for reprocessing alkanesulfonic acid. In this case it is preferable when the washing liquid is combined with the mother liquor.

Since crystallization of the alkanesulfonic acid causes high boilers to accumulate in the mother liquor particularly in the case of recycling into the distillation or the melt crystallization, it is moreover preferable when the mother liquor removed in step (c) is at least partly fed to a high boilers removal to remove high boilers from the mother liquor. After removal of the high boilers the mother liquor is recycled into the process for reprocessing alkanesulfonic acid. The feeding of the mother liquor into the high boilers removal and subsequent recycling into the process for reprocessing alkanesulfonic acid is referred to as the high boilers cycle. This high boilers removal is preferably effected before introduction of the mother liquor into the distillation for removing the low boilers or into the melt crystallization. It is particularly preferable when the mother liquor after removal of the high boilers is recycled into the distillation for removing the low boilers. This makes it possible for low boilers remaining in the mother liquor as impurities to likewise be removed from the mother liquor in the distillation. In an alternative option the mother liquor after removal of the high boilers is partly condensed and the condensed portion is recycled into the distillation for removing the low boilers and the uncondensed portion is discharged from the process as low boilers. In the case of recycling of the condensed portion of the mother liquor into the distillation for removing the low boilers the partial condensation of the mother liquor and the discharging of the uncondensed portion of low boilers reduces the proportion of low boilers to be removed in the distillation thus allowing the distillation as a whole to be configured for a reduced throughput which in turn makes it possible to make capital expenditure and, in particular, energy savings.

High boilers removal may be realized, for example, via an evaporation. This evaporates the low boilers present in the mother liquor, the alkanesulfonic acid and the high boilers remaining in the liquid phase. In order not to impair the alkanesulfonic acid and to allow the evaporation to be carried out at the lowest possible temperatures the evaporation is preferably carried out at a pressure below atmospheric pressure. The alkanesulfonic acid-comprising vapors formed during the evaporation may be condensed and returned as a liquid into the distillation for removing low boilers or into the melt crystallization in step (b) or, particularly preferably, into the chemical process. Condensation of the vapors also provides the option of removing low boilers. In this case the condensation is carried out such that the alkanesulfonic acid condenses while the low boilers remain in the gas phase. The alkanesulfonic acid-comprising liquid phase and the low boiler-comprising gas phase may then be separated in a gas-liquid phase separator and the low boilers present in the gas phase may be discharged from the process. An evaporation may also be facilitated by an entraining gas in the context of a stripping.

The high boiler-comprising fraction generated in the evaporation generally also comprises a proportion of alkanesulfonic acid which may optionally be recovered in a subsequent purification step.

Both the distillation for removing low boilers and the evaporation of the alkanesulfonic acid to remove high boilers are carried out at a pressure below atmospheric pressure. It is preferable when the distillation for removing low boilers and the evaporation to remove high boilers are carried out at a pressure in the range from 5 to 500 mbar (abs), preferably from 10 to 100 mbar (abs). This allows for distillation/evaporation that is gentle toward the alkanesulfonic acid product. At higher pressures the necessary temperatures for the distillation/evaporation would be of a magnitude such that product impairment, in particular decomposition of the alkanesulfonic acid, cannot be ruled out. It is known that distillation methods using entraining agents, so-called stripping methods, may be carried out at higher pressures. This procedure is regarded as equivalent to the use of reduced pressure in the context of the invention.

When the alkanesulfonic acid is methanesulfonic acid and pure methanesulfonic acid is to be crystallized the distillation for removing low boilers is to be carried out such that the starting melt has a concentration of at least 76 mol %, preferably at least 82 mol % and particularly preferably at least 90 mol %. The pressure and temperature settings for the distillation for removing low boilers may thus be varied within wide limits but are related to one another via substance-specific vapor pressure curves. The particularly preferred value for the methanesulfonic acid concentration in a methanesulfonic acid/water mixture of 90 mol % is achievable in a preferred pressure range of from 40 to 130 mbar and the corresponding bottoms temperature ranges of from 160° C. to 200° C. The reported temperature range is typically around 10 to 20 K higher than specified by physical substance-specific properties since flow in the column may give rise to pressure drops and insulation weaknesses may give rise to heat losses.

When the alkanesulfonic acid is methanesulfonic acid and methanesulfonic acid hydrate is to be crystallized, the distillation for removing low boilers is to be carried out such that the starting melt has a concentration of 31 to 75 mol %, preferably 45 to 63 mol % and particularly preferably 47 to 55 mol %. Here too, the pressure and temperature settings for the distillation for removing low boilers may be varied within wide limits. A particularly preferred value for the methanesulfonic acid concentration of 51 mol % is achievable, for example, at a pressure of from 40 to 130 mbar and a bottoms temperature of from 80° C. to 120° C.

When the alkanesulfonic acid is ethanesulfonic acid and pure ethanesulfonic acid is to be crystallized, the distillation for removing low boilers is to be carried out such that the starting melt has a concentration of at least 76 mol %, preferably at least 82 mol % and particularly preferably at least 90 mol %. The pressure and temperature settings for the distillation for removing low boilers may thus be varied within wide limits as in the production of methanesulfonic acid. Since ethanesulfonic acid has a markedly lower vapor pressure than methanesulfonic acid the preferred distillation pressures are correspondingly lower. An alternative increase of the distillation temperatures greatly in excess of 200° C. is problematic on account of appreciable ethanesulfonic acid decomposition.

When the alkanesulfonic acid is ethanesulfonic acid and ethanesulfonic acid hydrate is to be crystallized, the distillation for removing low boilers is to be carried out such that the starting melt has a concentration of from 31 to 75 mol %, preferably from 45 to 63 mol % and particularly preferably from 47 to 55 wt %.

The distillation may be performed in any desired distillation device known to those skilled in the art. The distillation is typically carried out in a distillation column which may comprise internals. Typical internals include, for example, trays or structured or unstructured packings. Useful trays include all known trays, for example sieve trays, bubble trays, tunnel trays or valve trays. Structured packings may be, for example, those made of ceramics materials or plastics materials such as PFTE or PFA. Unstructured packings are, for example, random packings and all commonly used packing elements may be employed, for example those made of ceramics materials, plastics materials such as PFTE or PFA.

The alkanesulfonic acid-comprising stream is generally introduced near the top of the distillation column. The low boilers are removed overhead and supplied to a workup or disposal. A material stream comprising alkanesulfonic acid, high boilers and residual low boilers, in particular water, is withdrawn at the bottom of the distillation column and fed to the melt crystallization as the starting melt. This starting melt is generally a monophasic liquid. This means that the alkanesulfonic acid too is completely comprised in the liquid phase.

Since the distillation and melt crystallization are carried out at different temperatures it is necessary, irrespective of the distillation device employed, to cool the alkanesulfonic acid-comprising material stream before it is fed to the melt crystallization. Even when the low boilers removal is carried out at the subatmospheric pressures indicated by way of example it is necessary to carry out the distillation with heating in order to establish a bottoms temperature in the range from 160° C. to 191° C. in the case of crystallization of pure methanesulfonic acid and in the range from 86° C. to 112° C. in the case of crystallization of methanesulfonic acid hydrate. Since, depending on the water content, the melting point of a methanesulfonic acid/water mixture is in the range from −54° C. to +20° C. appropriate cooling of the bottoms discharge preferably to a temperature just above the melting point of the starting melt must first be effected. Alternatively, it is also possible to supercool the melt before entry into the crystallizer. However such a mode of operation is not preferred since it is difficult to rule out unwanted crystallization in a heat exchanger. When a different alkanesulfonic acid is to be purified the temperatures must accordingly be matched to the boiling point/melting point of the alkanesulfonic acid.

The distillation for removing low boilers preferably frees the alkanesulfonic acid-comprising stream of low boilers to an extent such that, ignoring water, the proportion of impurities in the material stream comprising alkanesulfonic acid, high boilers and residual low boilers fed to the melt crystallization as the starting melt is not more than 6 wt %, preferably not more than 3 wt %, in the starting melt. It is particularly preferable when the proportion of impurities ignoring water is less than 2 wt %.

These indications are merely typical values which moreover depend on the chemical process in which the alkanesulfonic acid is employed and the high boilers content.

In contrast to the distillation which is carried out at a pressure below atmospheric pressure, the melt crystallization is generally effected at atmospheric pressure. In the case of pure methanesulfonic acid this melt crystallization is preferably carried out in the range from −10° C. to 19° C.

In order for the melt crystallization to afford pure methanesulfonic acid, i.e. methanesulfonic acid having a proportion of impurities and water of less than 1 wt %, preferably less than 0.5 wt % and in particular less than 0.2%, the melt crystallization is supplied with a material stream comprising alkanesulfonic acid, high boilers and residual low boilers which comprises at least 76 mol %, preferably at least 82 mol % and particularly preferably at least 90 mol % of methanesulfonic acid based on the total amount of methanesulfonic acid and water in the material stream comprising alkanesulfonic acid, high boilers and residual low boilers.

Before recycle streams are fed in, the material stream comprising alkanesulfonic acid, high boilers and residual low boilers moreover comprises not more than 6 wt %, preferably not more than 3 wt % and in particular not more than 2 wt % of impurities based on the total mass of the material stream comprising alkanesulfonic acid, high boilers and residual low boilers. When the substance mixture comprises impurities as well as water and alkanesulfonic acid, the molar concentration ratios of water to alkanesulfonic acid suitable for crystallization do not change substantially. Recycling in the high boilers cycle may cause the concentrations of impurities, for example of sulfuric acid, to exceed the reported values thus reducing the proportion of water. When higher concentrations of impurities are present lower crystallization temperatures are possible and necessary.

To obtain pure methanesulfonic acid the melt crystallization is carried out at a temperature in the range from −50° C. to 19° C. and preferably in the range from −10° C. bis 19° C., more preferably at a temperature in the range from −2° C. to 18° C. and in particular at a temperature in the range from 6° C. to 16° C. High crystallization temperatures are preferred since the energy requirements for the crystallization are thus lower than for lower crystallization temperatures.

To obtain the monohydrate of methanesulfonic acid in a melt crystallization, the material stream comprising alkanesulfonic acid, high boilers and residual low boilers fed to the melt crystallization as the starting melt comprises by preference 31 to 75 mol %, preferably 45 to 63 mol %, particularly preferably 47 to 55 mol % and in particular 48 to 52 mol % of methanesulfonic acid in each case based on the total amount of water and methanesulfonic acid in the material stream comprising alkanesulfonic acid, high boilers and residual low boilers. Here too the proportion of impurities is preferably not more than 6 wt %, more preferably not more than 3 wt % and in particular not more than 2 wt % based on the total mass of the material stream comprising alkanesulfonic acid, high boilers and residual low boilers. When the substance mixture comprises impurities as well as water and alkanesulfonic acid, the molar concentration ratios of water to alkanesulfonic acid suitable for crystallization do not change substantially. These indications are merely typical values which moreover depend on the MSA production method and the high boilers content. When high concentrations of impurities are present lower crystallization temperatures are possible and necessary.

The temperature at which the melt crystallization of the monohydrate of methanesulfonic acid is carried out is in the range from −50° C. to 12° C., preferably in the range from −15° C. to 12° C., more preferably in the range from −8° C. to 12° C. and in particular in the range from 0° C. to 12° C. High crystallization temperatures are preferred since they entail lower energy requirements for the crystallization.

The optimal crystallization conditions may vary depending on the type and concentration of the impurities. Said conditions should accordingly be determined by experiment for example. For low concentrations of impurities the crystallization conditions are very close to those for the pure two-substance mixture of water and methanesulfonic acid.

It has been found that both in the production of pure methanesulfonic acid and in the production of the hydrate of methanesulfonic acid a respective proportion of 6 wt % of sulfuric acid based on the total mass of the material stream comprising alkanesulfonic acid, high boilers and residual low boilers is noncritical and has but little effect on the crystallization conditions. It transpires for example that an impurity of 4 wt % of sulfuric acid in a mixture of water and methanesulfonic acid reduces the crystallization temperature of methanesulfonic acid by about 3° C. It further transpires for example that an impurity of 4 wt % of sulfuric acid in a mixture of water and methanesulfonic acid reduces the crystallization temperature of methanesulfonic acid by about 2° C.

The crystallizer in which the melt crystallization is carried out may be any apparatus suitable for performing a crystallization. Heat may be removed from the crystallizer by, for example, jacket cooling or by suitable internals, for example pipes through which a coolant flows, until a temperature low enough for crystallization is achieved. An example of a suitable coolant which in the case of jacket cooling flows through a double wall of the crystallizer or is employed in the throughflowed pipes is a mixture of water and ethylene glycol. It is alternatively possible to carry out direct cooling by means of an evaporating coolant, for example carbon dioxide.

In one embodiment, namely the suspension crystallization method, cooling in the crystallizer converts the starting melt into a suspension comprising alkanesulfonic acid crystals. To achieve this, solid crystals of alkanesulfonic acid may grow directly in the melt thus forming the suspension or alternatively the solid crystals may deposit as a layer on a cooled wall from which they are subsequently scraped off and resuspended in the mother liquor. Suitable apparatuses include, for example, stirred tanks, scraped surface coolers or disk crystallizers.

An alternative embodiment comprises carrying out a layer crystallization. Here, the crystallizate is formed as an uninterrupted adherent layer on a cooled surface of the crystallizer. In this case the solid-liquid separation is effected by flow-off of the mother liquor under gravity. The layer crystallization may be carried out either as a static layer crystallization or as a dynamic layer crystallization.

In static layer crystallization the starting melt is charged into a suitable heat exchanger, for example a tube bundle heat exchanger or a plate heat exchanger, and cooled by gradual temperature reduction to partly solidify the starting melt. In a further step the mother liquor is drained off and the temperature is increased again. This initially melts off a highly impurified fraction from the crystal layer before the product is melted off in high purity. However the disadvantage of the static crystallization method is the typically low space-time yield since heat and material transport to the deposition surfaces is effected only by free convection. By contrast, dynamic crystallization comprises establishing forced convection by pumped circulation of the mother liquor through fully throughflowed pipes, by introduction as a trickle film, by feeding inert gas into a pipe filled with mother liquor or by pulsing.

In suspension crystallization a suspension in which the crystals are suspended in the mother liquor is withdrawn from the crystallizer. Since alkanesulfonic acid is crystallized out of the starting melt the proportion of molten alkanesulfonic acid in the mother liquor withdrawn from the crystallizer is lower than that in the starting melt supplied to the crystallizer. The concentration of impurities in the mother liquor is also higher since these largely do not crystallize. Only the liquid portion, i.e. the liquid phase of the suspension, is referred to as mother liquor.

In order to remove the mother liquor and impurities adhering to the crystals it is possible and preferable to wash the crystals in step (d). This comprises contacting the crystals with a washing liquid with which the impurities are removed.

Any suitable washing means may be used to wash the crystals in step (d). It is possible here to employ a separate washing means or to carry out the solid-liquid separation and washing in one apparatus. One apparatus suitable therefor is, for example, a washing column. In the washing column the crystals to be purified and the washing liquid are preferably run in countercurrent. Since alkanesulfonic acids, in particular methanesulfonic acid, is corrosive it is necessary to configure not only the production apparatuses but also the crystallizer, the apparatus for solid-liquid separation and the washing means in such a way that they are process durable. It is in particular necessary to avoid the alkanesulfonic acid becoming contaminated by corroded and detached constituents of the apparatus. Suitable corrosion-resistant materials that may be used to fabricate the washing means include, for example, glasses, corrosion resistant steels, enameled steels or plastics materials. Plastics materials may be employed either as facing materials or in a loadbearing capacity. One suitable plastics material is, for example, high density polyethylene or else PTFE. Plastics materials are suitable primarily as a construction material or to provide corrosion insulation of the outer surface of the apparatus. It is possible that some apparatus parts may be under too high a level of mechanical stress for plastics materials. Construction may then be effected in such a way that the stressed plant parts are fabricated from, for example, mechanically stable, enameled steel.

Useful washing liquids include, for example, water, aqueous alkanesulfonic acid, sulfuric acid or other solvents. However, these all have the disadvantage that the crystals of alkanesulfonic acid may be dissolved. Impurities may also be introduced. It is therefore preferable to employ molten crystallizate as the washing solution instead of the abovementioned washing liquids. The molten crystallizate removes the mother liquor adhering to the crystals and the impurities. Since the molten crystallizate employed as the washing liquid becomes impurified by the mother liquor and by the impurities that are washed off from the crystals and the washing liquid comprises a large proportion of product of value on account of its composition it is preferable when the molten crystallizate employed as the washing liquid is recycled into the distillation for removing low boilers or into the melt crystallization after the washing.

When molten crystallizate is used as the washing liquid some of the washing liquid generally also crystallizes on the crystals to be purified.

In order to avoid sedimentation of the crystals from the suspension during transport between the individual apparatuses, in particular between the crystallizer and the washing means, it is preferable to homogenize the suspension. This may be achieved using stirrers or pumps for example. The washing means may either be directly supplied with the suspension withdrawn from the crystallizer while an alternative option comprises subjecting the suspension to processing before it is fed to the washing means. This comprises initially removing the crystals suspended in the mother liquor by mechanical means. This may be achieved using any known separation method for solid-liquid separations. Suitable separation methods include, for example, sieving, pressing, filtration, centrifugation, sedimentation and decantation. After removal of the mother liquor the crystals are resuspended in the washing liquid and the suspension is fed into the washing means.

When molten crystallizate is employed as washing liquid it is preferable when the temperature is selected such that the molten crystallizate for washing the crystals has a temperature 0.1° C. to 15° C. above the solidification temperature of the alkanesulfonic acid. It is preferable when the temperature of the crystallizate employed as washing liquid is 1° C. to 10° C. above the solidification temperature of the alkanesulfonic acid and in particular 2° C. to 4° C. above the solidification temperature of the alkanesulfonic acid.

The washing means is preferably operated such that the residence time of the crystals to be washed in the washer is in the range from 1 to 25 min and preferably in the range from 1 to 15 min. However, particularly but not exclusively when the suspension comprising crystals and the molten crystallizate washing liquid are run in countercurrent it has been found that sufficient purification efficacy is achieved even with a residence time of 2 to 8 min.

The crystals may be washed repeatedly to improve purification efficacy. To this end, the washing in step (d) or else the sequence comprising crystallization in step (b), solid-liquid separation in step (c) and washing in step (d) may be performed repeatedly or else operated with partial recycling. However, preference is given to performing crystallization and washing just once. The washing of the crystals may even be eschewed when product purity requirements are low.

The three cited material stream cycles, namely the distillation cycle, crystallization cycle and high boilers cycle pass through plant sectors which in some cases have very different temperature levels. In order to make good use of the energy introduced into the method while furthermore keeping the amount of energy required for heating and cooling the material streams as low as possible it is preferable when the material stream cycles are passed through heat transferrers which transfer heat in countercurrent. For example, the material stream withdrawn from the bottoms discharge of the low boilers distillation and comprising alkanesulfonic acid, high boilers and residual low boilers and high boilers is cooled before being fed to the melt crystallization while, conversely, the alkanesulfonic acid-depleted mother liquor recycled into the distillation is heated. It is thus particularly preferable when heat from the material stream comprising alkanesulfonic acid, high boilers and residual low boilers and high boilers which is to be cooled is transferred to the alkanesulfonic acid-depleted mother liquor which is to be heated.

When efficient crystallization and washing methods are available the low boilers and high boilers may be accumulated to high concentrations in the high boilers cycle, i.e. in the recirculating mother liquor, without the crystallized alkanesulfonic acids failing to meet industry purity specifications. Total amounts of low boiler and high boiler impurities in the starting melt of up to 8 wt % may be tolerated without issue. This allows the stream volumes that are passed through large temperature differences in the high boilers cycle to be kept sufficiently small for the heating and cooling requirements thereof to be small compared to the heat requirements in any case necessitated in process engineering terms. The method according to the invention accordingly requires less energy than conventional methods.

The chemical process in which the alkanesulfonic acid is employed is, for example, an alkylation or an esterification reaction. However, in addition to these two reaction types, further reactions carried out in the presence of an acidic catalyst are also conceivable. It is particularly preferable when the chemical process is an alkylation of salicylic acid or of substituted or unsubstituted aromatics. The method according to the invention is very particularly suitable for the reprocessing of methanesulfonic acid employed as catalyst in the production of linear alkylbenzene from benzene or substituted benzene with an olefin.

The alkanesulfonic acid employed in the chemical process and reprocessed as per the method according to the invention is in particular methanesulfonic acid.

Working examples of the invention are shown in the figures and are more particularly described in the description which follows.

FIG. 1 shows a process flow diagram for a chemical process with a reprocessing of alkanesulfonic acid by crystallization.

Figure 1:
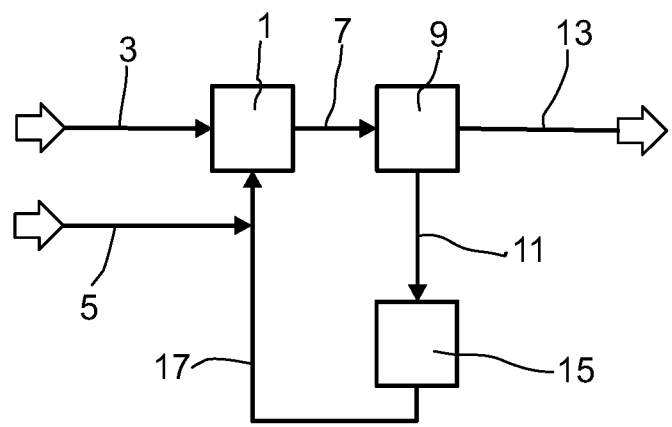
FIG. 1 shows a process flow diagram of a reprocessing of alkanesulfonic acid by crystallization.

A chemical process 1, for example an alkylation for producing linear alkylbenzenes, is supplied with reactants 3. In the production of linear alkylbenzenes the employed reactants 3 are typically unsubstituted or substituted benzene and linear olefins. These reactants 3 may comprise further additions, for example solvent. Since the reaction proceeds in the presence of a catalyst a catalyst must be added in addition to the reactants 3. In accordance with the invention the catalyst is alkanesulfonic acid, in particular methanesulfonic acid.

An alkanesulfonic acid-comprising reaction mixture 7 is withdrawn from the chemical process 1. The reaction mixture 7 is fed to a separator 9. In the separator 9 the reaction mixture is separated into an alkanesulfonic acid-comprising stream 11 and a crude product stream 13. In addition to the product produced in the chemical process, for example linear alkylbenzene, the crude product stream 13 typically further comprises reactants, solvents and possibly byproducts formed during the reaction. A small proportion of alkanesulfonic acid may also still be present.

In accordance with the invention the alkanesulfonic acid-comprising stream 11 is fed to a crystallizer 15 and purified by crystallization because the alkanesulfonic acid-comprising stream 11 still comprises impurities which upon direct recycling into the chemical process 1 could have deleterious repercussions, in particular in the form of an activity loss of the alkanesulfonic acid employed as catalyst.

In the crystallizer the alkanesulfonic acid-comprising stream 11 is supplied as starting melt and cooled in order that the alkanesulfonic acid crystallizes. The crystallizate is withdrawn, optionally washed, melted and recycled back into the chemical process as return 17.

Losses of alkanesulfonic acid which may arise, for example, due to removal with the crude product stream 13 or due to removal of impurities from the crystallization may be compensated via a catalyst feed 5. This may comprise feeding the alkanesulfonic acid via the catalyst feed 5 either into the return 17 as depicted here or else directly into the chemical process 1.

Figure 2:
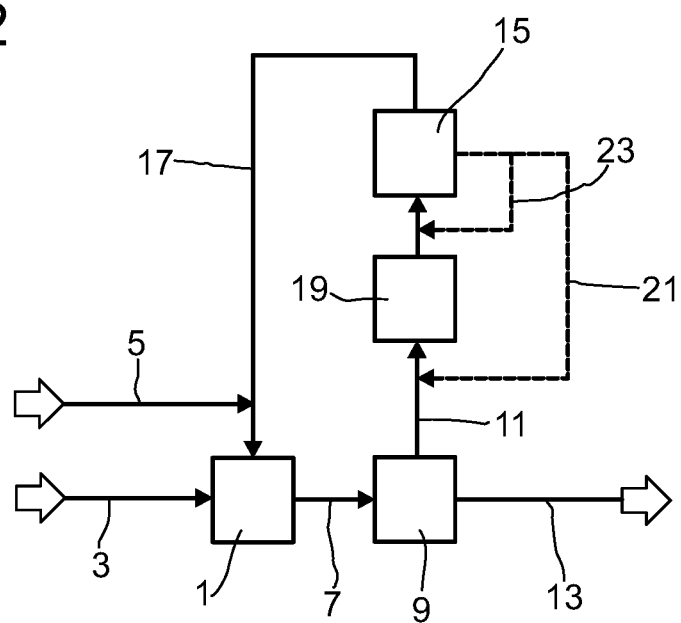
FIG. 2 shows a process flow diagram of a reprocessing of alkanesulfonic acid by crystallization with low boilers removal.

FIG. 2 shows a process flow diagram of a reprocessing of alkanesulfonic acid by crystallization with low boilers removal.

In contrast to the embodiment depicted in FIG. 1, the embodiment depicted in FIG. 2 further comprises a low boilers removal 19. In this case the alkanesulfonic acid-comprising material stream 11 withdrawn from the separator 9 is initially fed into the low boilers removal 19. In the low boilers removal 19 low boilers present as impurities are removed from the alkanesulfonic acid-comprising material stream preferably by distillation. After removal of the low boilers the alkanesulfonic acid-comprising material stream is then fed as the starting melt into the crystallizer 15 in which the alkanesulfonic acid crystallizes.

Alkanesulfonic acid-comprising mother liquor not crystallized in the crystallizer 15 may be entirely or partly recycled into the low boilers removal 19 via a first recycle 21. Alternatively or in addition, it is also possible to entirely or partly recycle the mother liquor into the crystallizer 15 via a second recycle 23. However, recycling into the low boilers removal 19 is preferred since previously unremoved low boilers may also accumulate in the mother liquor.

In addition to the low boilers removal 19 a high boilers removal is also advantageous. Said removal is not depicted in FIGS. 1 and 2 and is preferably effected downstream of the crystallization. To effect high boilers removal it is possible, for example, to distil the uncrystallized mother liquor from the crystallizer 15, thus evaporating the alkanesulfonic acid present in the mother liquor. The high boilers thus remain in the bottoms in the liquid phase. The evaporated alkanesulfonic acid may be condensed and recycled into the chemical process 1. Alternatively, recycling into the low boilers removal 19 is also possible. This has the advantage that low boilers present in the mother liquor which are likewise converted into the gas phase during the distillative high boilers removal may still be removed. It is moreover also possible to recycle the alkanesulfonic acid after condensation into the crystallizer 15 as per the second recycle 23. However, preference is given to introducing the condensed alkanesulfonic acid from the high boilers removal into the chemical process 1 or the low boilers removal 19.

Figure 3:
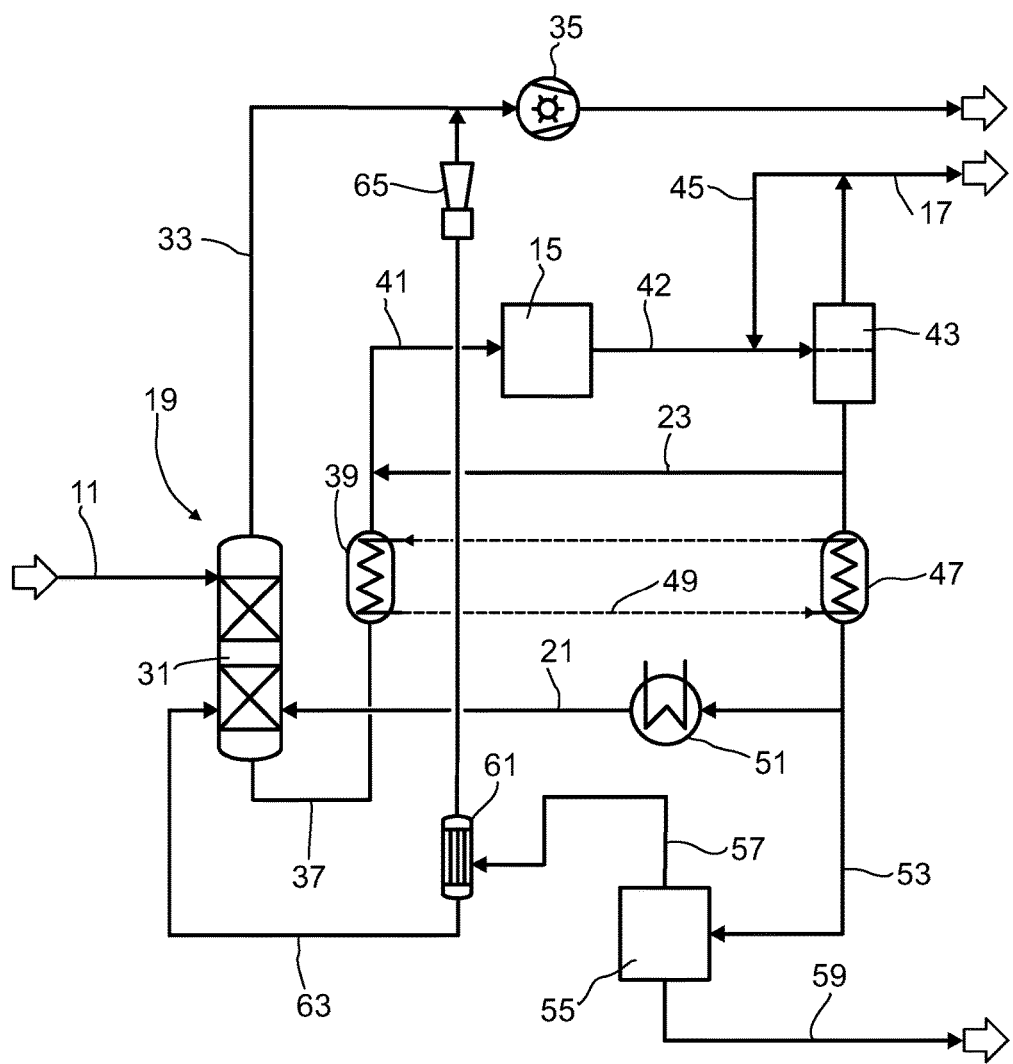
FIG. 3 shows a process flow diagram of a reprocessing of methanesulfonic acid by distillation and crystallization.

FIG. 3 depicts a process flow diagram of a reprocessing of an alkanesulfonic acid using methanesulfonic acid as an example by distillation and crystallization.

An alkanesulfonic acid-comprising stream 11 removed from a chemical process is fed to a low boilers removal 19. The low boilers removal 19 is effected for example as depicted here by distillation. To this end, the alkanesulfonic acid-comprising stream 11 is introduced to the upper region of a distillation column 31. The distillation column 31 for low boilers removal may comprise suitable internals. Internals that may be provided include, for example, trays or packings as are known to those skilled in the art. Suitable trays include, for example, sieve trays, bubble-cap trays, tunnel-cap trays or perforated trays. Packings used may be structured or random packings. Random packings generally comprise packing elements, for example Raschig® rings, Pall rings, saddles, Berl saddles, cylindrical packing elements or any other shape of packing elements. In the low boilers removal 19 the alkanesulfonic acid-comprising material stream is brought to a concentration suitable for crystallization.

At the top of the distillation column 31 low boilers, in particular water, are drawn off as tops stream 33. The tops stream 33 is passed through a pump 35, for example a liquid ring pump, with which the desired pressure for the distillation is generated. The tops stream 33 is subsequently drawn off out of the process and worked up separately or disposed of.

At the bottom of the distillation column 31 an alkanesulfonic acid-comprising bottoms stream 37 is drawn off. The distillation establishes a concentration of water in the bottoms stream 37 such that the bottoms stream 37 comprises a crystallizable concentration of alkanesulfonic acid.

Since the crystallization is carried out at a temperature substantially lower than the bottoms temperature in the distillation the bottoms stream 37 is cooled in a first heat transferrer 39. After cooling in the first heat transferrer the bottoms stream is fed to the crystallizer 15 as starting melt 41. The crystallization may be carried out as a layer crystallization or else as a suspension crystallization. In the process depicted here by way of example the crystallization is a suspension crystallization.

A suspension 42 of crystals of the alkanesulfonic acid and mother liquor is withdrawn from the crystallizer 15 and fed to a solid-liquid separation and a washing means 43 in which the alkanesulfonic acid crystals are removed and washed to remove the mother liquor and impurities adhering thereto. To this end it is possible, for example, to run the alkanesulfonic acid crystals suspended in mother liquor in countercurrent to a washing liquid, for example molten crystallizate. The washing liquid washes off the mother liquor and impurities from the crystals. After separation of the crystals from the washing liquid by a solid-liquid separation method purified alkanesulfonic acid is obtained and withdrawn from the process and returned into the chemical process via the return 17.

Some of the purified alkanesulfonic acid may be melted and returned via a conduit 45 as washing liquid.

The washing liquid comprising mother liquor and impurities is likewise withdrawn from the apparatus for solid-liquid separation and washing means 43 as an alkanesulfonic acid-depleted stream. Since this material stream still comprises a large proportion of alkanesulfonic acid, said stream is preferably not removed from the process.

It is thus possible, for example, to recycle the washing liquid and alkanesulfonic acid-depleted material stream withdrawn from the washing means 43 into the melt crystallization 9 via the second recycle 23. This may comprise recycling either the entire stream or merely a substream.

To counter an impermissible level of accumulation of low boilers in this recycle, the washing liquid and the alkanesulfonic acid-depleted stream withdrawn from the washing means may be recycled into the distillation column 31 for low boilers removal 19 via the first recycle 21. This is advisable particularly when pure alkanesulfonic acid rather than the monohydrate of alkanesulfonic acid is obtained in the crystallizer 15. By contrast, in the crystallization of the monohydrate a suitable low boilers concentration may alternatively be established by adjusting the bottoms temperature of the distillation column 31 employed for low boilers removal 19. It will be appreciated that another option comprises recycling a substream of the material stream comprising the washing liquid and alkanesulfonic acid-depleted mother liquor into the low boilers removal 19 via the first recycle 21 and a further substream into the crystallizer 15 via the second recycle 23.

In the embodiment depicted in FIG. 3 the alkanesulfonic acid-depleted material stream withdrawn from the washing means 43 is fed into a second heat transferrer 47. A suitable coupling of the first heat transferrer 39 and the second heat transferrer 47 utilizes the low temperature of the alkanesulfonic acid-depleted material stream withdrawn from the washing means 43 to cool the alkanesulfonic acid-comprising bottom stream 37 withdrawn from the low boilers removal. As a result of the severe corrosivity of the alkanesulfonic acid direct heat transfer from the hot stream to the cold stream is possible only with a high level of technical complexity, if at all. The bottoms stream 37 accordingly gives off heat to a heat transfer medium in the first heat transferrer 39. The heat transfer medium flows via a heat transfer medium circuit 49 into the second heat transferrer 47 in which said medium gives off the previously absorbed heat to the alkanesulfonic acid-depleted material stream withdrawn from the washing means 43, thus heating said stream. The cooled heat transfer medium then flows back into the first heat transferrer 39 via the heat transfer medium circuit 49.

Since the distillation for low boilers removal is carried out at a very much higher temperature than the crystallization, the first recycle 21 is moreover provided with a third heat transferrer 51 in which the recycled alkanesulfonic acid-depleted material stream is heated to the temperature required for recycling into the low boiler removal 19.

To remove high boilers from the alkanesulfonic-acid-depleted material stream withdrawn from the washing means 43, at least some of the mother liquor, the so-called high boilers purge 53, is fed to an evaporator 55. Alternatively, the high boilers purge 53 may also be directly disposed of. However, disposal is advisable only when a large part of the mother liquor has been returned to the purification process via the first recycle 21 and/or the second recycle 23. In the evaporator 55 alkanesulfonic acid and low boilers are evaporated and drawn off as vapors 57. The unevaporated portions are withdrawn from the evaporator in liquid form as worked up high boilers purge stream 59 and supplied for further use or disposal.

The vapors 57 withdrawn from the evaporator 55 are recycled either into the low boilers removal 19 as depicted here or, preferably after condensation, into the chemical process. In the embodiment depicted here the vapors 57 flow into a partial condenser 61. In the partial condenser 61 the alkanesulfonic acid present in the vapors condenses and is recycled into the low boilers removal 19 as condensate 63. Without partial condensation the vapors can only with difficulty be passed directly into the low boilers removal 19 in gaseous form because the evaporator 55 and the distillation column 31 employed for low boilers removal 19 are typically operated at different pressure levels. An alternative recycling option for the condensed vapors is use, after cooling, as washing liquid for the washing means 43.

The uncondensed portion comprising low boilers is withdrawn from the partial condenser 61 in gaseous form and drawn off from the process together with the low-boilers-comprising material stream 33 from the distillation column 31.

To reduce the pressure of the condensate 63 that is returned into the distillation column 31 a jet pump 65 may be provided in the material stream withdrawn in gaseous form from the partial condenser 61. As an alternative to a jet pump it is also possible to employ any other apparatus known to those skilled in the art with which a gas may be conveyed and reduced pressure generated. The use of the jet pump 65 reduces the pressure in the partial condenser 61 and the condensate 63 therefore also exits the partial condenser 61 at a pressure lower than the pressure in the evaporator 55.

For reasons of energy economy it is advisable to use the smallest possible high boilers purge 53. The lower limit for reducing the amount of high boilers purge 53 is the amount at which just sufficient amounts of high boilers are still discharged from the cycle to keep the concentration of said high boilers below the concentration above which they impede crystallization.

EXAMPLES

Example 1

To produce dodecylbenzene with 100% methanesulfonic acid as catalyst, 164 g of benzene, 50 g of 1-dodecene and 283 g of n-octane together with 769 g of methanesulfonic acid (Lutropur® 100 from BASF SE) were charged into a double-walled glass reactor of 2.5 l in volume. The glass reactor was provided with a stirrer, a condenser and a thermocouple. The experiment was performed under an argon inert gas atmosphere. After stirring the solution for 2 minutes at 1000 rpm the stirrer was stopped. A phase separation occurred within about 120 seconds. Once the phases had separated, a start sample of the organic phase was taken. The reaction mixture was subsequently heated to 60° C. over 30 minutes with stirring at 1000 rpm and then stirred for a further five hours at this temperature. After each hour the stirrer was briefly stopped and, after phase separation, a sample of the organic phase was taken. Once reaction had ended the stirrer was stopped and the reaction mixture was cooled to room temperature. This caused the phases to separate. The upper hydrophobic phase was clear and colorless. The lower, methanesulfonic acid-containing phase exhibited slight brown discoloration. This phase was drained off. This affords 428 g of hydrophobic phase and 777 g of hydrophilic, methanesulfonic acid-containing phase. The samples of organic phase were analyzed by gas chromatography to monitor the progress of the reaction. The decline in the dodecene concentration and the formation of dodecylbenzene isomers were observed. The areas of the GC signals for the dodecene isomers, for the dodecylbenzene isomers and for n-octane were measured and the dodecene isomers/octane and dodecylbenzene isomers/octane ratios were calculated. To observe the decline in the dodecene concentration, concentrations were normalized to the value of the start sample.

Examples 2 to 8

The examples describe the production of dodecylbenzene with recycling of the hydrophilic, methanesulfonic acid-containing phase.

The experiments were performed similarly to example 1. However, instead of the 769 g of fresh methanesulfonic acid, the hydrophilic, methanesulfonic acid-containing phase from the preceding experiment was employed. Losses of methanesulfonic acid arising from sampling and analysis of the phase were replaced with fresh 100% methanesulfonic acid. Thus, after the experiment described in example 1 and the analysis of the methanesulfonic acid-containing hydrophilic phase, 748 g of the hydrophilic phase remained. To compensate for the loss, 21 g of 100% methanesulfonic acid were added to this amount.

Appearance, methanesulfonic acid content and water content of the hydrophilic phase after the experiments are reported in table 1.

After seven recycling cycles the hydrophilic phase was yellow/brown and the hydrophobic product phase exhibited a reddish color. The experiments show that during the methanesulfonic acid-catalyzed reaction of dodecene with benzene, colored compounds are formed which accumulate in the methanesulfonic acid-containing hydrophilic phase. When these components are not removed, recycling of the methanesulfonic acid results in the hydrophobic dodecylbenzene-comprising phase likewise becoming discolored.

It has been found that the water content in the reaction mixture increased slightly for each recycling. Analysis of the respective hourly sampled organic phases revealed that a water content in the methanesulfonic acid-containing phase of more than 0.25 wt % results in a significant drop in catalytic activity.

Examples 9 to 12

Examples 9 to 12 describe the production of dodecylbenzene with different water concentrations in the methanesulfonic acid-containing phase.

The experiments were performed similarly to example 1. However, a small amount of water was added to the methanesulfonic acid before each experiment. After phase separation of the reaction mixture the water content in the hydrophilic, methanesulfonic acid-containing phase was analyzed. The water contents for the individual experiments are likewise reported in table 1.

The conversion curves for dodecene in the experiments and the formation of dodecylbenzene clearly show the impact of water on the catalytic activity of the methanesulfonic acid. Here too, the conversion declined appreciably with increasing water content.

TABLE 1

Composition of the hydrophilic phase

| Example | Methanesulfonic acid recycling from example | Methanesulfonic acid content of the hydrophilic phase (wt %) | Water content of the hydrophilic phase (wt %) | Appearance |
|---|---|---|---|---|
| 1 | start | 97.6 | 0.10 | slightly yellowish |
| 2 | 1 | 97.4 | 0.12 | yellowish |
| 3 | 2 | 97.3 | 0.15 | |
| 4 | 3 | 97.4 | 0.17 | yellow color |
| 5 | 4 | 97.2 | 0.25 | becomes more |
| 6 | 5 | 97.2 | 0.27 | intense |
| 7 | 6 | 97.0 | 0.29 | |
| 8 | 7 | 97.1 | 0.43 | yellow/brown |
| 9 | — | n.d. | 0.30 | slightly yellowish |
| 10 | — | n.d. | 0.39 | slightly yellowish |
| 11 | — | n.d. | 0.60 | slightly yellowish |
| 12 | — | n.d. | 1.10 | slightly yellowish | n.d.: not determined

Example 13

The example describes the production of dodecylbenzene and the distillative removal of the water from the hydrophilic phase.

164 g of benzene, 50 g of 1-dodecene and 94 g of n-octane together with 765.2 g of methanesulfonic acid (Lutropur® 100 from BASF SE) and 3.8 g of water (corresponding to 0.5 wt % of water in the hydrophilic phase) were charged into a double-walled glass reactor of 2.5 l in volume. The glass reactor was provided with a stirrer, a condenser and a thermocouple. The experiment was performed under an argon inert gas atmosphere. After mixing the solution for 2 minutes at 1000 rpm the stirrer was stopped. Once the phases had separated, a start sample of the organic phase was taken. The reaction mixture was subsequently heated to 80° C. over 45 minutes with stirring at 1000 rpm and then stirred for a further five hours at this temperature. After each hour the stirrer was briefly stopped and, after phase separation, a sample of the organic phase was taken. Once reaction had ended the stirrer was stopped and the reaction mixture was cooled to room temperature. This caused the phases to separate. The lower, methanesulfonic acid-containing phase had a slight yellow discoloration. This phase was drained off. This affords 233 g of hydrophobic phase and 772 g of hydrophilic, methanesulfonic acid-containing phase. The phases were analyzed as described under example 1.

757 g of the slightly yellow hydrophilic phase having a water content of 0.7 wt % were incipiently distilled in a rotary evaporator at 160° C. at a pressure of 4 mbar (abs). 34 g of distillate were collected in the receiver flask. The bottoms darken during the distillation. Once the distillation had ended 689 g of yellow hydrophilic phase remained in the bottoms. The remaining hydrophilic phase had a water content of 0.05 wt %.

Examples 14 to 21

Examples 14 to 21 describe the production of dodecylbenzene with recycled hydrophilic phase after distillative removal of the water in a laboratory apparatus.

The experiments were performed similarly to the description of example 13. However, in place of the 765.2 g of fresh methanesulfonic acid, the hydrophilic, methanesulfonic acid-containing phase from the preceding experiment was employed. Losses of methane sulfonic acid arising from sampling and analysis of the phase were replaced by 100% methanesulfonic acid.

After carrying out example 19 and chemical analysis of the methanesulfonic acid-containing hydrophilic phase, 675 g of the hydrophilic phase remained. To compensate for losses 90.2 g of 100% methanesulfonic acid were added to this amount.

The distillation parameters from example 19 are described here by way of example. 780.6 g of hydrophilic phase were employed in this experiment. The bottoms temperature at the end of the distillation was 143° C. The overhead temperature was 135° C. at an overhead pressure of 2 mbar. 25.3 g of a first tops fraction comprising mainly benzene and 58.0 g of a second tops fraction comprising essentially water and methanesulfonic acid were obtained. The bottoms underwent severe dark discoloration during the distillation. The bottoms had a water concentration of 0.4 wt % (by Karl-Fischer titration). The bottoms (677.3 g) were employed in experiment 21. The methanesulfonic acid losses were compensated with 100 wt % methanesulfonic acid.

After experiment 21 and phase separation, 236.8 g of a cloudy hydrophobic phase exhibiting slight brownish discoloration and 775.6 g of a slightly hydrophilic methanesulfonic acid-containing phase exhibiting dark brown discoloration were obtained.

After repeated distillation the color of the hydrophilic methanesulfonic acid-containing phase darkened severely. Finely divided solids particles were also formed. In the hydrophobic phase too, colored components resulted in appreciable darkening.

The experiments show that under the conditions of a distillation methanesulfonic acid undergoes chemical reaction with reaction products from the LAB process. The reaction products from the reaction of methanesulfonic acid are very dark and upon repeated distillation, in particular at temperatures above 150° C., may form insoluble particles or oils.

Although the distillation conditions for removing the water were below 145° C., the reaction of the methanesulfonic acid with aromatic olefins was unavoidable. Although lowering the distillation pressure in principle allows for distillation at lower temperatures with reduced formation of impurities, this method requires very low pressures, for example below 10 mbar, which correspondingly entail more cost and complexity.

The reaction products formed indicate that a distillation, which results in very low water concentrations of less than 1 wt % in the recycled methanesulfonic acid, is an unsuitable process step in a recycled LAB process. Accordingly, distillation is not a suitable means for recycling methanesulfonic acid.

Example 22

The example describes the production of dodecylbenzene with recycled hydrophilic phase from experiment 21.

The experiment was conducted similarly to Example 1. However, in place of the 769 g of fresh methanesulfonic acid, the hydrophilic, methanesulfonic acid-containing phase (681 g) from example 22 was employed. To compensate for the loss, 88 g of 100% methanesulfonic acid were added to this amount. However, in contrast to example 1, the phase separations in these experiments did not occur within 120 seconds but rather required at least 10 minutes. Once reaction had ended an intermediate phase formed between the very dark hydrophilic phase and the brownish hydrophobic phase. All three phases were isolated. The intermediate phase separated into a hydrophobic phase and a hydrophilic phase only after being left to stand for a lengthy period of several hours This example shows that surface-active and color-conferring compounds can form and accumulate in the hydrophilic phase.

Example 23

The example describes the production of dodecylbenzene with 100% methanesulfonic acid as catalyst.

78.7 g of benzene, 24.0 g of 1-dodecene and 135.8 g of n-octane together with 370 g of methanesulfonic acid purified by crystallization were charged into a double-walled glass reactor of 2.5 l in volume. The glass reactor was provided with a stirrer, a condenser and a thermocouple. The experiment was performed under an argon inert gas atmosphere. After a short period of mixing the stirrer was stopped. A phase separation occurred within about 30 seconds. Once the phases had separated, a sample of the organic phase was taken. Subsequently, the reaction mixture was heated to 60° C. with stirring and the mixture was stirred for a further five hours. After each hour the stirrer was briefly stopped and, after phase separation, a sample of the organic phase was taken. Once reaction had ended the stirrer was stopped and the reaction mixture was cooled to room temperature. This caused the phases to separate. The upper hydrophobic phase was clear and colorless. The lower, methanesulfonic acid-containing phase was cloudy and exhibited slight brown discoloration. Said phase was drained off and analyzed for water content. It comprised 0.22 wt % of water.

Example 24

The example describes the production of dodecylbenzene with methanesulfonic acid that has been purified by crystallization.

78.7 g of benzene, 24.0 g of 1-dodecene and 135.8 g of n-octane together with 370 g of methanesulfonic acid purified by crystallization (from example 25) were charged into a double-walled glass reactor of 2.5 l in volume. The glass reactor was provided with a stirrer, a condenser and a thermocouple. The experiment was performed under an argon inert gas atmosphere. After a short period of mixing the stirrer was stopped. A phase separation occurred within about 30 seconds. Once the phases had separated, a sample of the organic phase was taken. Subsequently, the reaction mixture was heated to 60° C. with stirring and the mixture was stirred for a further five hours. After each hour the stirrer was briefly stopped and, after phase separation, a sample of the organic phase was taken. Once reaction had ended the stirrer was stopped and the reaction mixture was cooled to room temperature. This caused the phases to separate. The upper hydrophobic phase was clear and colorless. The lower, methanesulfonic acid-containing phase was cloudy and exhibited slight brown discoloration. Said phase was drained off and analyzed for its water content. It comprised 0.15 wt % of water. Comparison of the progress of the reaction for example 23 and example 24 showed no deviation.

Example 24 shows that methanesulfonic acid may be purified by crystallization to an extent such that it achieves a quality suitable for recycling into a methanesulfonic acid-catalyzed process.

Example 25

The example describes the crystallization of methanesulfonic acid from the impurified methanesulfonic acid-containing phase from the production of linear alkylbenzene.

Low boilers and water were removed by distillation from 1510 g of impurified methanesulfonic acid from a laboratory-simulated production of linear alkylbenzene to achieve a residual concentration of water of 0.35 wt % at a pressure under conditions identical to example 19. The very dark bottoms from the distillation column were then charged into a 1 liter double-walled stirred vessel of 150 mm in diameter fitted with a close-clearance helical stirrer. The mixture was then cooled from 15° C. to 2.8° C. at a cooling rate of 1 K/h. The temperature was measured in the mixture with an immersed PT100 thermocouple. During cooling crystals formed in the mixture, these being kept in suspension by stirring at 250 rpm. The obtained crystals in the suspension were removed on a pressure filter at about 3.5 bar within less than 1 minute. The mother liquor from the crystallization was collected. The crystallizate was washed with pure methanesulfonic acid in a 1:1 ratio and then melted. The washing solution was likewise collected separately. The molten crystallizate is a colorless liquid having a water content of 0.10 wt %.

The obtained mother liquor from the crystallization, the washing filtrate and the washed, molten crystallizate were analyzed with a PerkinElmer Lambda 900® UV/Vis spectrometer. The reference employed was highest-purity water from a Millipore Milli-Q® reference water installation having a resistance in excess of 18.2 MΩ and a TOC content of less than 5 ppb.

The spectral analysis was carried out at room temperature at a scan rate of 267 nm/min with an integration time of 0.20 seconds, a data interval of 1 nm, a slit width of 2 nm and a wavelength range of 200 to 800 nm in a fused silica cuvette of 0.1 cm in diameter.

The spectral analysis yielded the following extinctions at 400 nm:

| | |
|---|---|
| mother liquor from the crystallization | $E_{400} = 1.9$ |
| washing filtrate | $E_{400} = 0.8$ |
| crystallizate | $E_{400} = 0.03$ |

It is clearly apparent from the absorption spectra obtained that color-giving components generated by nongentle distillation conditions may be virtually completely removed from methanesulfonic acid by crystallization. A comparison of the water values for starting material and methanesulfonic acid crystallizate shows that low boilers such as water may also be removed from the methanesulfonic acid by crystallization.

Example 26

The example describes the purification of methanesulfonic acid by crystallization to remove water.

A methanesulfonic acid starting melt having a methanesulfonic acid content of 96 wt % and a content of 3.0 wt % of water and further impurities and a temperature of 15° C. was charged at atmospheric pressure into a jacketed stirred vessel of 1 l in volume and 150 mm in diameter fitted with a close-clearance helical stirrer. The starting melt was then cooled to 6.5° C. at a cooling rate of 1 K/h. The temperature was measured in the starting melt with a PT100 thermocouple. Crystals were formed during cooling, these being kept in suspension by stirring at 150 rpm. The obtained crystals in the suspension were removed on a pressure filter at about 3.5 bar within less than 1 minute. The mother liquor from the crystallization was collected. The crystallizate was washed with pure methanesulfonic acid in a 1:1 ratio and then melted. The washing solution was likewise collected separately. The molten methanesulfonic acid crystallizate has a water content of 0.27 wt %.

The example shows that crystallization is a suitable method of removing water from a methanesulfonic acid-water mixture.

LIST OF REFERENCE NUMERALS

1 chemical process
3 reactants
5 catalyst feed
7 reaction mixture
9 separator
11 alkanesulfonic acid-comprising stream
13 crude product stream
15 crystallizer
17 return
19 low boilers removal
21 first recycle
23 second recycle
31 distillation column
33 tops stream
35 pump
37 bottoms stream
39 first heat transferrer
41 starting melt
42 suspension
43 washing means
45 conduit
47 second heat transferrer
49 heat transfer medium circuit
51 third heat transferrer
53 high boilers purge
55 evaporator
57 vapors
59 high boilers purge stream
61 partial condenser
63 condensate
65 jet pump

The invention claimed is:

1. A method of reprocessing alkanesulfonic acid employed in a chemical process as an agent, catalyst or solvent, the method comprising:
 (a) removing an alkanesulfonic acid-comprising stream from a reaction mixture generated in the chemical process,
 (b) feeding the alkanesulfonic acid-comprising stream into a melt crystallization as a starting melt to form crystals of the alkanesulfonic acid, of hydrates of the alkanesulfonic acid or of a mixture of both suspended in a mother liquor,
 (c) performing a solid-liquid separation to remove the crystals from the mother liquor,
 (d) optionally washing the crystals to remove the mother liquor adhering to the crystals, and
 (e) recycling the washed or unwashed crystals removed from the mother liquor into the chemical process.

2. The method according to claim 1, wherein the reaction mixture in (a) is biphasic and the alkanesulfonic acid-comprising stream is removed from the reaction mixture by phase separation.

3. The method according to claim 1, wherein the mother liquor after removal of the crystals in (c) and/or the mother liquor generated in (b) are at least partly recycled into the melt crystallization in (b).

4. The method according to claim 1, wherein
 the alkanesulfonic acid-comprising stream before being fed into the melt crystallization in (b) is distilled to remove low boilers,
 the low boilers are drawn off at the top of a distillation column,
 a material stream comprising the alkanesulfonic acid, high boilers and residual low boilers is withdrawn at the bottom of the distillation column, and
 the stream comprising the alkanesulfonic acid, the high boilers and the residual low boilers is fed to the melt crystallization in (b).

5. The method according to claim 4, wherein the mother liquor after removal of the crystals in (c) and/or the mother liquor generated in (b) are at least partly recycled into the melt crystallization or into the distillation column for removing low boilers.

6. The method according to claim 1, wherein the crystals from (c) or from (d) are fed to a distillation for water removal.

7. The method according to claim 1, wherein the mother liquor after removal of the crystals in (c) and/or the mother liquor generated in (b) are at least partly fed to a high boilers removal in which the alkanesulfonic acid is removed by evaporation.

8. The method according to claim 7, wherein the alkanesulfonic acid removed by evaporation is recycled into the chemical process.

9. The method according to claim 8, wherein the alkanesulfonic acid removed by evaporation is at least partially condensed before being recycled into the chemical process.

10. The method according to claim 7, wherein
the mother liquor after removal of the high boilers is partially condensed to obtain a condensed portion and an uncondensed portion,
the condensed portion is recycled into a distillation for removing the low boilers or into the melt crystallization in (b), and
the uncondensed portion is discharged from the process as low boilers.

11. The method according to claim 1, wherein the alkanesulfonic acid is methanesulfonic acid.

12. The method according to claim 1, wherein the chemical process is an alkylation or an esterification reaction.

13. The method according to claim 1, wherein the chemical process is an alkylation of salicylic acid or of substituted or unsubstituted aromatics.

14. The method according to claim 13, wherein the chemical process is production of linear alkylbenzene from benzene or substituted benzene with an olefin in the presence of the alkanesulfonic acid as a catalyst.

15. The method according to claim 1, wherein the melt crystallization is a suspension crystallization or a layer crystallization.

\* \* \* \* \*

UNITED STATES PATENT AND TRADEMARK OFFICE
CERTIFICATE OF CORRECTION

PATENT NO. : 10,214,485 B2
APPLICATION NO. : 15/774722
DATED : February 26, 2019
INVENTOR(S) : Jan Spielmann et al.

Page 1 of 1

It is certified that error appears in the above-identified patent and that said Letters Patent is hereby corrected as shown below:

In the Specification

In Column 23, Line 29, "hours" should read -- hours. --.

Signed and Sealed this
Twenty-third Day of July, 2019

Andrei Iancu
*Director of the United States Patent and Trademark Office*